United States Patent [19]

Hagishita et al.

[11] Patent Number: 5,073,648
[45] Date of Patent: Dec. 17, 1991

[54] 4-(4-ALKOXYPHENYL)-2-BUTYLAMINE DERIVATIVE AND PROCESS THEREFOR

[75] Inventors: Sanji Hagishita, Nara; Kaoru Seno, Hyogo, both of Japan

[73] Assignee: Shionogi & Co., Ltd., Osaka, Japan

[21] Appl. No.: 645,737

[22] Filed: Jan. 25, 1991

[30] Foreign Application Priority Data

Feb. 23, 1990 [JP] Japan ................................ 2-43547

[51] Int. Cl.$^5$ ............................................ C07C 217/54
[52] U.S. Cl. .................................... 564/374; 564/398
[58] Field of Search ..................... 564/374, 375, 398

[56] References Cited

U.S. PATENT DOCUMENTS

| | | | |
|---|---|---|---|
| 2,276,618 | 3/1942 | Kulz | 564/381 |
| 3,493,662 | 2/1970 | Duerr | 564/374 |
| 3,987,200 | 10/1976 | Tuttle et al. | 514/654 |
| 4,105,695 | 8/1978 | Partyka et al. | 564/375 |
| 4,663,351 | 5/1987 | Diamond | 514/548 |
| 4,704,407 | 11/1987 | Massey | 564/374 |
| 5,011,996 | 4/1991 | Kiel et al. | 564/374 |

FOREIGN PATENT DOCUMENTS

| | | | |
|---|---|---|---|
| 0893341 | 9/1953 | Fed. Rep. of Germany | 564/374 |
| 0153366 | 1/1982 | German Democratic Rep. | 564/374 |
| 3917279 | 8/1964 | Japan | 564/374 |

OTHER PUBLICATIONS

Redlinski, Adam et al, "Preparation of 3-amino-1-(-4-methoxyphenyl)butane as intermediate for dobutamine", CA, 110, 94675p (1989).

Primary Examiner—Glennon H. Hollrah
Assistant Examiner—Susan P. Treanor
Attorney, Agent, or Firm—Wenderoth, Lind & Ponack

[57] ABSTRACT

This invention relates to an optically active (+)-secondary amine of the formula:

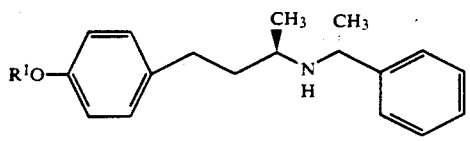

wherein $R^1$ is a lower alkyl, and to a process for preparing a useful intermediate for the production of the optically active dopamine derivatives, namely, optically active (+)-primary amine of the formula:

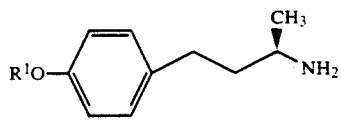

wherein $R^1$ is a lower alkyl, characterized by the reduction of said optically active (+)-secondary amine.

1 Claim, No Drawings

4-(4-ALKOXYPHENYL)-2-BUTYLAMINE DERIVATIVE AND PROCESS THEREFOR

BACKGROUND OF THE INVENTION

1. Field of the Invention

This invention relates to a process for preparing optically active (+)−primary amines (I) of the formula:

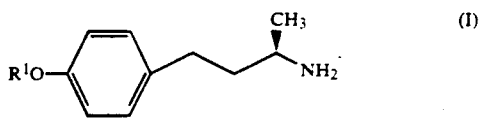

wherein $R^1$ is lower alkyl, which are useful intermediates for the production of the optically active dopamine derivatives (I), e.g., dobutamine. It further relates to key intermediates for the amines and the process therefor.

2. Prior Art

Dobutamine has been developed by Eli Lilly and Company and denoted by the following formula:

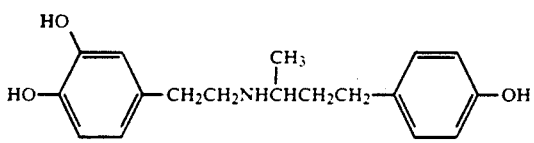

This compound is very useful, because it can increase myocardial contractility without isolating norepinephrine. The recemate, the 1:1 mixture of d-isomer and l-isomer is clinically applied to the patients for the treatment of suddenly depressed myocardial contractility and shock.

There are two kinds of optical isomers in dobutamine and the optically active dobutamine have been prepared via optical resolution of the intermediate as disclosed in U.S. Pat. No. 3,987,200.

SUMMARY OF THE INVENTION

This invention provides an optically active (+)−secondary amine of the formula:

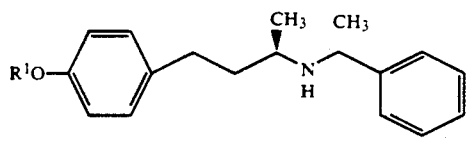

wherein $R^1$ is a lower alkyl, and to a process for preparing optically active (+)−primary amine (I) of the formula:

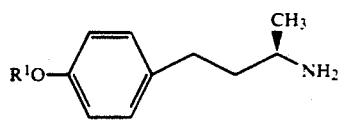

wherein $R^1$ is a lower alkyl, characterized by the reduction of said optically active (+)−secondary amine. The optically active amine (I) is a useful intermediate for the production of optically active dopamine derivatives.

DETAILED DESCRIPTION OF THE INVENTION

It has been reported that the d-isomer (hereinafter described as d-dobutamine) has more potent activity as a cardiotropic than the l-isomer (hereinafter described as l-dobutamine) has. Therefore, it is desired to prepare only d-dobutamine.

However, the conventional method is not economical since the optical resolution has been applied to the final intermediate for dobutamine preparation, namely, trimethyl ether compound. It is needless to say that the economical preparation of the aimed optically active compound can be achieved by obtaining an optically active intermediate at an earlier stage in a series of the reactions and applying it to the subsequent reactions.

The present inventors studied hard to solve the above mentioned problem.

As a result, they found that the reaction of (+)-α-methyl-benzylamine with compound (II) of the formula:

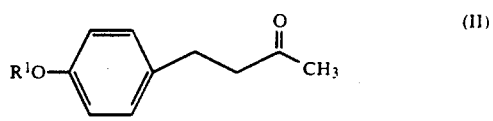

wherein $R^1$ is the same as defined above, and the subsequent reduction gives an optically active (+)−secondary amine (III) of the formula:

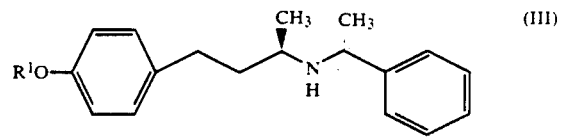

wherein $R^1$ is the same as defined above, in high yield and the subsequent reduction of the resulting amine gives an useful intermediate of d-dobutamine, namely, optically active (+)−primary amine (I) of the formula:

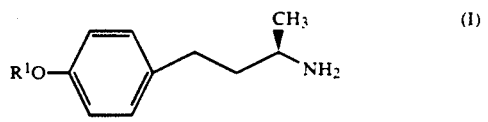

wherein $R^1$ is the same as defined above.

As described afterward, the compound (I) is a very important intermediate in preparation of d-dobutamine. Moreover, the compound (III) is very important as a starting material for the production of compound (I).

In this specification, lower alkyl shown by $R^1$ includes $C_1$-$C_6$ alkyl, e.g., methyl, ethyl, propyl, isopropyl, butyl, tert-butyl, pentyl, hexyl, or the like.

Preferable $R^1$ is methyl and ethyl.

This invention is explained below in more detail.

As an asymmetric synthesis to prepare an optically active secondary amine (III) by the reaction of (+)-α-methylbenzylamine with the compound (II), there are the following two methods: (A) in one batch system, the reduction of the resulting Schiff base with a reducing catalyst such as nickel catalysts (e.g., Raney nickel), platinium oxide, or palladium-carbon, or the like, preferably, with nickel catalyst under an atmosphere of hydrogen, preferably, with a positive pressure or (B) the reduction of the Schiff base prepared through a dehydration condensation with a reducing catalyst such as nickel catalysts (e.g., Raney nickel), platinium oxide, or palladium-carbon, or the like, preferably with nickel catalyst under an atmosphere of hydrogen, preferably with a positive pressure.

The aimed asymmetric synthesis can be also attained if metal hydride such as sodium borohydride is employed.

The reduction may be carried out in an alcohol, e.g., methanol, ethanol, or the like or an ester, e.g., ethyl acetate, or the like under a mild pressure such as about 1 to about 20 Kg/cm$^2$, preferably, about 3 to about 10 Kg/cm$^2$. If necessary, acetic acid may be added.

The reaction time varis with the reaction conditions employed but could be several hours to several days for method (A) and several ten hours for method (B). The reaction system is contaminated with a by-product i.e., small amount of diastereomer of the compound (III) in the reduction, but can readily give the aimed optically active secondary amine through fractional cystallization from acetone and methanol-ethyl acetate.

The product prepared by the reduction may be isolated, if necessary, after converting into its desirable acid addition salt by treating with a mineral acid, e.g., hydrochloric acid, hydrobromic acid, phosphoric acid, sulfuric acid, or the like.

The condensation is preferably carried out by the refluxe with benzene or toluene with an equipment to entrap the resulting water.

An optically active amine (I) can be prepared by the reduction of the compound (III) under an atmosphere of hydrogen, preferably with a positive pressure.

The reaction is carried out by the reduction under about 2 to 20 Kg/cm$^2$ of hydrogen pressure for several tens hours using catalyst such as palladium-carbon, palladium hydroxide, platinum oxide, or the like in an alcohol such as methanol, ethanol, or the like.

Alternatively, the reaction may be carried out with heating for several hours in the presence of ethyl chlorocarbonate.

This invention is explained in more detail by showing examples, but it should be understood that these examples are given only for the illustrative purpose and do not limit the scope of the present invention thereto.

EXAMPLE 1A

Method (A)

Preparation of
N-(R)-α-methylbenzyl-(1R)-1-methyl-3-(4-methoxyphenyl)-1-propylamine hydrochloride IIIa

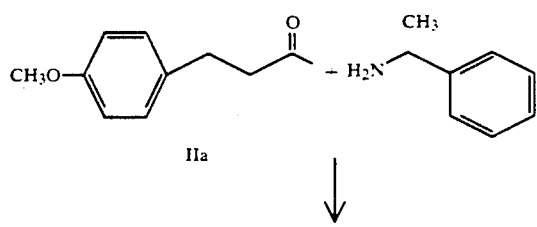

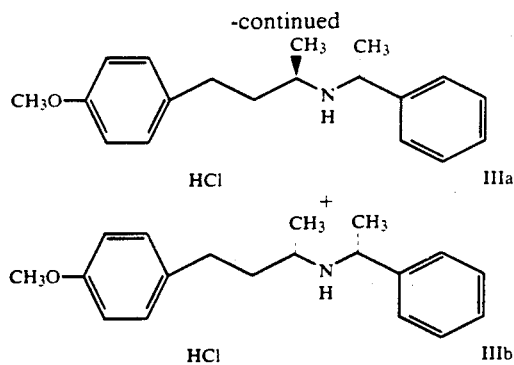

A mixture of 13.6 g of 4-(4-methoxyphenyl)-2-butanone IIa, 11.5 g of d-(+)-α-methylbenzylamine, and 1 g of Raney-nickel (Kawaken Finechemical; NDHT-90) in 90 ml of 98% ethanol is shaken at 4.85 Kg/cm$^2$ primary pressure for 5 days. The catalyst is removed by filtration and the filtrate is concentrated under reduced pressure. The residue is partitioned between dichloromethane and 10% diluted hydrochloric acid. The dichloromethane layer is washed with water, dried over anhydrous sodium sulfate, and concentrated under reduced pressure to give 14.9 g of the mixture of diastereomers IIIa and IIIb in the ratio of 6.7:1 in yield 60.9%. 74% d.e.

EXAMPLE IB

Method (B)

A solution of 1.78 g of 4-(4-methoxyphenyl)-2-butanone and 1.21 g of d-(+)-α-methylbenzylamine in benzene is refluxed for 5 hours under heating with removing resulting water and then the solvent is evaporated under reduced pressure.

The mixture of the resulting residue and 0.3 g of Raney-Nickel in 10 ml of 98% ethanol is shaken at 4.5 kg/cm$^2$ primary pressure for 22 hours. The catalyst is removed by filtration and the filtrate is concentrated under reduced pressure. The residue is partitioned between dichloromethane and 10% hydrochloric acid. The dichloromethane layer is washed with water, dried over anhydrous sodium sulfate, and concentrated under reduced pressure to give 2.14 g of the mixture of diastereomers IIIa and IIIb in the ratio of 5.8:1 in yield 66.9%.

Isolation of the Diastereomers IIIa and IIIb

To 2.14 g of the mixture prepared in Example 1B is added 20 ml of acetone and the resulting mixture is heated and then allowed to stand at room temperature for 2 hours. The precipitates ① (71 mg) are collected by filtration. The solvent of the filtrate is changed to methanol-ethyl acetate (1:4) and the solution is allowed to stand at room temperature overnight to give ② 1.321 g of the crystals. The resulting mother liquor was successively recrystallized from acetone and methanol-ethyl acetate (1:4) to give ③ 63 mg and ④ 256 mg of crystals, respectively. The crystals ① and ③ are the compound IIIb and the crystals ② and ④ are IIIa.

Compound IIIa

100% d.e.
mp. 157° to 158° C.
$[\alpha]_D + 69.6°$ (c 1.117, methanol)
IRνmax(nujol) 2930, 1253cm$^{-1}$ NMR(CDCl$_3$) δ1.51(3H, d, J=7 Hz), 1.88(3H, d, J=7 Hz), 2.11(2H, m), 2.32(1H, m), 2.72(2H, m), 3.78(3H, s), 4.29(1H, m), 6.75(2H, d, J=9 Hz), 6.95(2H, d, J=9 Hz), 7.34(3H, m), 7.54(2H, m), 9.64(1H, m), 10.00(1H, m).

Anal. Calcd. (%) for C$_{19}$H$_{26}$ClNO: C, 71.34; H, 8.19; Cl, 11.08; N, 4.38; Found (%): C, 71.30; H. 8.16; Cl, 11.11; N, 4.47.

Compound IIIb m.p. 257° to 258° C.
[α]$_D$−3.4°, [α]$_{365}$−18.1° (c 0.976, 24° C., methanol)
IRνmax(nujol): 2950, 2930, 1240cm$^{-1}$
NMR(CDCl$_3$) δ: 1.35(3H, d, J=6 Hz), 1.82 (3H, d, J=7 Hz), 1.8~2.1(1H, m), 2.3~2.6(3H), 2.35(1H, m), 3.70(3H, s), 4.29(1H, m), 6.66(2H, d, J=7 Hz), 6.94(2H, d, J=9 Hz), 7.39(3H), 7.62(2H), 9.51(1H, m), 10.04(1H, m).

Anal. Calcd. (%) for C$_{19}$H$_{26}$ClNO: C, 71.34; H, 8.19; Cl, 11.08; N, 4.38; Found (%): C, 71.14; H, 8.15; Cl, 10.79; N, 4.40

EXAMPLE 2

(+)-(R)-1-Methyl-3-(4-methoxyphenyl)-1-propylamine Ia

A suspension of 3.20 g of hydrochloride IIIa in ethyl acetate is shaken with an aqueous solution of sodium hydrogencarbonate. The organic layer is separated and the aqueous layer is extracted with ethyl acetate. The combined organic layer is washed with water once, dried over anhydrous sodium sulfate, and concentrated under reduced pressure. The residue is dissolved in 40 ml of ethanol and 0.8 g of 20% palldium hydroxide-carbon (Pearlman Catalyst) is added thereto. The mixture is shaken at 4.15 Kg/cm$^2$ hydrogen pressure for 20 hours. The catalyst is removed by filtration and then the mother liquor is concentrated under reduced pressure to give 1.68 g of the titled compound.

NMR(CDCl$_3$) δ1.11(3H, d, J=6 Hz), 1.5~1.7(4H, m), 2.62(2H, m), 2.91(1H, m), 3.78(3H, s), 6.82(2H, d, J=7 Hz), 7.11(2H, d, J=8 Hz).

Hydrochloride of Ia: mp. 124°-125° C.
[α]$_D$+7.0°, [α]$_{365}$+23.6° (c 1.029, 24° C., methanol)
IRνmax(nujol): 3500, 3350, 1513, 1244cm$^{-1}$.

NMR(CD$_3$OD) δ: 1.33(3H, d, J=7 Hz), 1.87 (2H, m), 2.65(2H, m), 3.25(1H, m), 3.76(3H, s), 6.85(2H, d, J=9 Hz), 7.14(2H, d, J=8 Hz).

Anal. Calcd. (%) for C$_{11}$H$_{18}$ClNO.0.2H$_2$O: C, 60.24; H, 8.46; Cl, 16.16; N, 6.39; Found (%): C, 60.40; H, 8.49; Cl, 16.38; N, 6.66.

Anti-IIIb (1.11 g), namely, the enantiomer of IIIb prepared by reacting l-α-methylbenzylamine in the same manner as in Example 1A is allowed to react in the same manner as in Example 2 to give 0.53 g of hydrochloride Ia in 85.2% yield.

EXAMPLE 3 d-(+)-α-Methylbenzylamine and the compound IIa is allowed to react by the method in Example 1A under the conditions shown in Table 1 to give the compound IIIa. The results is also shown in Table 1.

TABLE 1

| No. | Catalyst | Hydrogen Pressure [kg/cm$^2$] | Reaction Time | Reaction Tempt. | Solvent | Yd. (%) | Produced Ratio IIIa:IIIb |
|---|---|---|---|---|---|---|---|
| 1 | Raney-Nickel | 4.5 | 2.5 day | rt. | Ethanol | 42.2 | 6.1:1 |
| 2 | " | 1 | 15 hrs | rt. | " | 35.0 | 6.6:1 |
| 3 | Platinum Oxide | 1 | 4 hrs | rt. | Methanol-Acetic Acid | 79.7 | 2.8:1 |

EXAMPLE 4 d-(+)-α-Methylbenzylamine and the compound IIa is allowed to react by the method in Example 1B under the conditions shown in Table 2 to give the compound IIIa. The results is also shown in Table 2.

TABLE 2

| No. | Catalyst or Reducing Agent | Hydrogen Pressure [kg/cm$^2$] | Reaction Time | Reaction Tempt. | Solvent | Yd. (%) | Produced Ratio IIIa:IIIb |
|---|---|---|---|---|---|---|---|
| 1 | 10% Pd-C | 4.85 | 16 hrs | rt. | Ethyl Acetate | 56.0 | 2.0:1 |
| 2 | Sodium Borohydride | — | 2 hrs | 0° C. | Methanol | 78.2 | 1.8:1 | rt. Room Temperature

In the following referencial example, the preparation of d-dobutamine from the optically active primary amine Ia is shown.

Referencial Example 1

(1) Preparation of (−)-(R)-2-(3,4-dimethoxyphenyl)-N-(4-methoxyphenyl-1-methyl-n-propyl)acetamide 4

To a solution of 2.08 g of 3,4-dimethoxyphenylacetic acid in 22 ml of dichloromethane is added 0.86 ml of thionyl chloride. After the mixture is refluxed for 1 hour under heating, the reaction mixture is concentrated to be half volumn under reduced pressure.

To 20 ml of suspension of 1.90 g of hydrochloride Ia in dichloromethane is added 5 ml of triethylamine with ice-cooling. The mixture is stirred at room temperature till the solide becomes disappear. To the resulting solution is dropwise added the solution of the acid chloride prepared above with ice-cooling. The mixture is allowed to stand at room temperature overnight, then washed with water, and dried over anhydrous sodium sulfate and the solvent is evaporated under reduced pressure. The residue is recrystallized from ethyl acetate: ether to give 2.48 g of the titled compound in 78.8% yield.

mp. 116°-117° C.
[α]$_D$−31.2° (c 1.057, 24° C., CHCl$_3$)
IRνmax(nujol): 3290, 1638, 1514, 1230 cm$^{-1}$.

NMR (CDCl₃) δ: 1.09(3H, d, J=7 Hz), 1.63 (2H, m), 2.49(2H, t, J=8 Hz), 3.49(2H, s), 3.78(3H, s), 3.87(3H, s), 3.89(3H, s), 4.01(1H, m), 5.19(1H, d, J=8 Hz), 6.73~6.9(5H), 7.02(2H, d, J=9 Hz).

Anal. Calcd. (%) for C₂₁H₂₇NO₄: C, 70.56; H, 7.61; N, 3.92; Found(%): C, 70.59; H, 7.66; N, 3.99.

(2) Preparation of (+)-(R)-3,4-dimethoxy-N-[3-(4-methoxyphenyl)-1-methyl-n-propyl]-2-phenylethylamine hydrochloride 5

To a solution of 1.92 g of amide 4 and 1.01 g of sodium borohydride in 22 ml of dioxane is dropwise added a solution of 1.61 g of glacial acetic acid in 5 ml of dioxane and the mixture is refluxed for 18 hours under heating. The ice-water is added to the reaction mixture which is then extracted with chloroform. The extract is washed with water once, drided over anhydrous sodium sulfated, and concentrated under reduced pressure. The residue is crystallized from ether to give 1.30 g of the titled compound in 63.7% yield.

mp. 144°-146° C.
[α]$_D$+9.8° (c 0.997, 25° C., methanol),
[α]$_{365}$+35.4° (c 0.997, 25° C., methanol),
IRνmax(nujol) 1516, 1246 cm⁻¹
NMR (CDCl₃) δ1.48(3H, d, J=6 Hz), 2.21 (2H, m), 2.35(1H, m), 2.55(2H, m), 2.63(2H, m), 3.15(4H), 3.72(3H, s), 3.83(3H, s), 3.85 (3H, s), 6.7–6.85(5H), 7.0(2H, d, J=9 Hz).

Anal. Calcd. (%) for C₂₁H₃₀ClNO₃: C, 66.39; H, 7.96; Cl, 9.33; N, 3.69; Found (%): C, 65.67; H, 8.04; Cl, 9.07; N, 3.96.

(3) Preparation of (+)-(R)-3,4-dihydroxy-N-[3-(4-hydroxyphenyl)-1-methyl-n-propyl]-2-phenylethylamine hydrochloride 6

A solution of 364 mg of the above mentioned trimethoxy compound 5 in dichloromethane is shaken with 10% aqueous solution of sodium hydroxide. The organic layer is washed with water, dried over anhydrous sodium sulfate, and concentrated to give 312 mg of the free amine.

A solution of this free amine is 9.5 ml of glacial acetic acid and 37 ml of 48% hydrobromic acid is refluxed for 4 hours under heating. The reaction mixture is evaporated to dryness under reduced pressure.

To the residue is added 15 ml of 4N-hydrochloric acid and the mixture is heated and then the reaction mixture is treated with active carbon. The resulting mixture is allowed to stand at room temperature overnight to give 203 mg of colorless prismatic crystals in 62.7% yield.

mp. 201°–203° C.
[α]$_D$+10.8° (c 0.930, 24° C., Methanol)
[α]$_D$+39.5° (c 0.930, 24° C., Methanol)
IRνmax(nujol): 3310, 1516cm⁻¹.
NMR(CD₃OD) δ1.36(3H, d, J=7 Hz), 1.79(1H, m), 2.04(1H, m), 2.45~2.95(4H), 3.10~3.30(3H), 6.57(1H, dd, J=8.2 Hz), 6.65~6.80 (4H), 7.04(2H, d, J=8 Hz).

Anal. Calcd. (%) for C₁₈H₂₄ClNO₃: C, 63.99; H, 7.16; Cl. 10.49; N, 4.15; Found (%): C, 63.92; H, 7.22; Cl. 10.78; N, 4.22.

What is claimed is:

1. An optically active (+)—secondary amine of the formula:

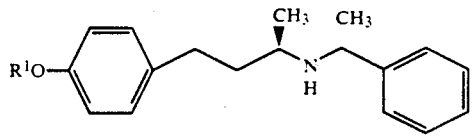

wherein R¹ is lower alkyl, or acid addition salt thereof.

* * * * *